United States Patent [19]

Bays

[11] Patent Number: 4,644,951
[45] Date of Patent: Feb. 24, 1987

[54] VACUUM SLEEVE FOR A SURGICAL APPLIANCE

[75] Inventor: F. Barry Bays, Seminole, Fla.

[73] Assignee: Concept, Inc., Clearwater, Fla.

[21] Appl. No.: 776,439

[22] Filed: Sep. 16, 1985

[51] Int. Cl.$^4$ ............................................. A61F 17/32
[52] U.S. Cl. ..................................... 128/305; 604/22; 128/753
[58] Field of Search .................. 604/902, 22; 128/304, 128/305, 752–755, 758

[56] References Cited

U.S. PATENT DOCUMENTS

| | | | |
|---|---|---|---|
| 3,769,980 | 11/1973 | Karman | 128/304 |
| 4,311,140 | 1/1982 | Bridgman | 128/304 |
| 4,522,206 | 6/1985 | Whipple et al. | 604/22 |

Primary Examiner—C. Fred Rosenbaum
Assistant Examiner—J. L. Kruter
Attorney, Agent, or Firm—Frijouf, Rust & Pyle

[57] ABSTRACT

A vacuum sleeve is disclosed for removing severed tissue from a surgical site. The vacuum sleeve is used in conjunction with a surgical appliance having a cutting element and the vacuum sleeve is connected to a vacuum source. The vacuum sleeve includes an elongated body member having a distal and a proximal end. The body member defines an internal passageway which extends between the distal and proximal ends of the body member. The internal passageway removably receives therein the surgical appliance and the distal end of the body member defines a aperture such that when the surgical appliance is disposed within the internal passageway, the cutting element of the surfical appliance extends through the aperture thereby enabling the cutting element to sever tissue from the surgical site. The internal passageway is connected to a vacuum source such that in use of the surgical appliance, when tissue is severed from the surgical site, the severed tissue is drawn from the surgical site through the aperture and along the internal passageway towards the source of vacuum.

18 Claims, 16 Drawing Figures

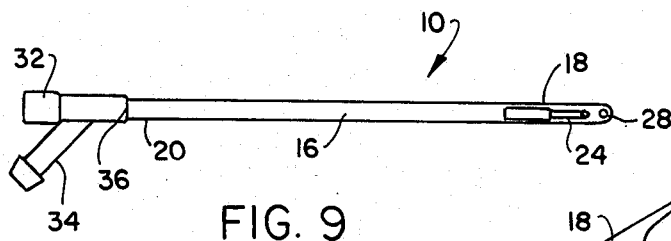
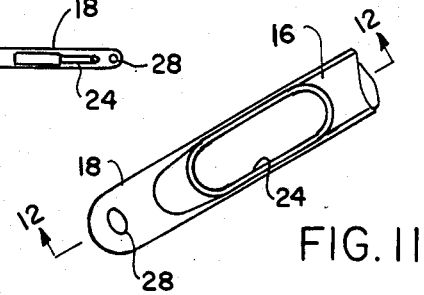
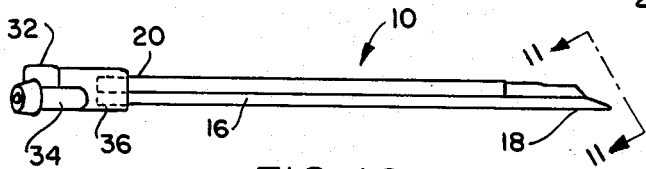
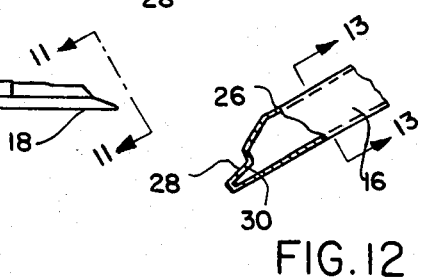
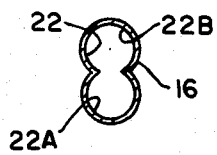
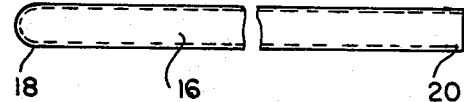

VACUUM SLEEVE FOR A SURGICAL APPLIANCE

BACKGROUND OF THE INVENTION

1. Field of the Invention

This invention relates to a vacuum sleeve for use with a surgical appliance. More particularly, this invention relates to a vacuum sleeve for removing severed tissue from the surgical site for use with a surgical appliance having a cutting element and for connection to a vacuum source or the like.

2. Information Disclosure Statement

Surgical instruments have been developed which enable a surgeon to resect tissue from a surgical site. Usually such surgical instruments include a scissor-like handpiece for reciprocating a distal cutter relative to a stationary jaw.

In operation of such resection devices, it is usual for the surgeon to insert the distal portion of the surgical appliance within the surgical site and then to pivot the scissor arms in order to move the cutter relative to the jaw for cutting small portions of tissue from the surgical site. Instruments of the aforementioned type have many applications in the surgical art but have particular application in the art of knee joint surgery or arthroscopy. Many variations of the aforementioned concept have been proposed including instruments in which the distal end is curved in various directions in order to provide ease of access to the surgical site.

As will be appreciated by those skilled in the art, when tissue is removed from the surgical site, it is necessary that such removed tissue be carried away from the cutter. Therefore, in order to assist in the removal of such tissue, surgical tools have been developed that have a hollow tubular member extending between the cutter towards the handle of the appliance so that when vacuum is applied to the hollow tubular member, tissue is drawn away from the distal end of the appliance.

However, in view of the multiplicity of angular configurations of the tubular member that are required in order to successfully carry out such resection, it has been necessary to equip an operating theater with a very large number of variously-shaped resection appliances, each of which must be provided with a relatively complex vacuum drainage system.

The present invention seeks to overcome the aforementioned problem and associated expense by providing a flexible sleeve which may be slipped over the top of surgical appliances of various angular configurations. The vacuum sleeve includes a passageway attached to a source of vacuum such that tissue may be removed from the cutter away from the surgical site.

The primary advantage of the aforementioned flexible vacuum sleeve, is the avoidance of the need of a multiplicity of costly resection tools including relatively complex hollow tubular members for the extraction of the removed tissue.

U.S. Pat. No. 2,751,908 to Wallace teaches a surgical instrument for enabling a surgeon to remove a polyp from the wall of a nasal passage. The instrument includes a pair of scissor-like hand grips, a tubular extension and a cutter and jaw disposed at the distal end of the extension. In operation of the device, when the cutter is disposed adjacent the polyp to be removed and with suction applied to a flexible conduit extending from adjacent the handle to the jaw, the surgeon blocks an air passage in the flexible conduit thereby creating a suction at the distal end of the instrument adjacent to the polyp. The polyp is then drawn by the suction effect towards the cutter and the surgeon is able to remove the polyp by actuating the cutter relative to the jaw. With the polyp removed by the cutter, the surgeon removes the obstruction from the vacuum tube and removes the surgical instrument from the nasal passage.

The aforementioned patent teaches the use of a controlled vacuum source in order to draw a polyp towards the cutter but does not teach the removal of the polyp along and through the vacuum tube.

The present invention is directed towards the provision of a surgical instrument for progressively removing tissue from a surgical site as such particles of tissue are cut from the site. Such particles of tissue are removed without the necessity for removing the distal end of the surgical instrument from the surgical site.

Therefore, it is the primary object of the present invention to provide a vacuum sleeve for removing severed tissue from a surgical site for use with a surgical appliance having a cutting element. The vacuum sleeve is used with a plurality of surgical instruments having various angular configurations.

Another object of the present invention is the provision of a vacuum sleeve for use with a surgical appliance having a cutting element. The vacuum sleeve is flexible thereby enabling the sleeve to slide over a plurality of differently shaped instruments.

Another object of the present invention is the provision of a vacuum sleeve for removing severed tissue from a surgical site, the vacuum sleeve being discarded after use.

Another object of the present invention is the provision of a vacuum sleeve for removing severed tissue from a surgical site for use with a surgical appliance in which the sleeve includes an input aperture disposed in the distal end of an elongated body member for facilitating the flow of tissue severed from the surgical site along an internal passageway of the body member.

Another object of the present invention is the provision of a vacuum sleeve for a surgical appliance in which the body member is of a unitary plastic material thereby reducing the cost of the same.

Another object of the present invention is the provision of a vacuum sleeve for a surgical appliance in which the internal passageway of the body member frictionally receives the surgical appliance therein.

Another object of the present invention is the provision of a vacuum sleeve for a surgical appliance in which the end wall of the body member forms an angle relative to the body member to facilitate insertion of the vacuum sleeve into the surgical site.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the invention. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The vacuum sleeve of the present invention is defined by the appended claims with a specific embodiment shown in the attached drawings. For the purpose of summarizing the invention, the invention relates to an externally applied adapter sleeve means and move particularly to an adapter vacuum sleeve for removing severed tissue from a surgical site for use with a self-contained cutting instrument such as a surgical appliance having a cutting element and for connection to a vacuum source. The vacuum sleeve includes an elongated body member having a distal end and a proximal end. The body member defines an internal passageway means which extends between the distal and proximal ends of the body member. The internal passageway removably receives therein the surgical appliance and the distal end of the body member defines an aperture such that when the surgical appliance is disposed within the internal passageway, the cutting element of the surgical appliance extends through the cutting aperture enabling the cutting element to sever tissue from the surgical site. The internal passageway is connected to the vacuum source such that in use of the surgical appliance, when tissue is severed from the surgical site, the severed tissue is drawn from the surgical site through the aperture and along the internal passageway of the elongated body member towards the source of vacuum.

In a more specific embodiment of the present invention, the elongated body member is of flexible plastics material having a unitary construction such that the body member is able to accommodate therein a surgical appliance having a curved configuration. The internal passageway of the body member is formed for frictionally receiving the surgical appliance therein and the sleeve defines an aperture which is disposed in a sidewall of the body member, the sidewall being located in proximity to the distal end of the body member. The distal end of the body member also includes an input aperture for facilitating the flow of tissue severed from the surgical site along the internal passageway of the body member. The flow of tissue is established from the surgical site into the input aperture and through the internal passageway of the body member. The sleeve also includes an end wall which is disposed along the distal end of the body member such that the aperture is disposed in a sidewall of the body member and the input aperture is disposed in the end wall of the body member. The end wall forms an angle relative to the elongated body member to facilitate insertion of the vacuum sleeve into the surgical site. The proximal end of the vacuum sleeve defines a seal port for receiving the surgical appliance therein. The seal port is flexible for resiliently engaging the surgical appliance extending through the internal passageway of the elongated body member at the proximal end of the body member. The vacuum sleeve also includes a vacuum port in fluid communication with the internal passageway of the elongated body member. The vacuum port is connectable to the vacuum source for removing tissue severed from the surgical site. The removed tissue is drawn through the aperture and along the internal passageway by the action of the vacuum source. Additionally, the vacuum sleeve includes a vacuum coupling for coupling the vacuum port such that the vacuum port is in fluid communication with the vacuum source. Furthermore, the internal passageway of the body member has a non-circular figure-8 cross-section for receiving the surgical appliance therein.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 9 is a top plan view of the surgical sleeve according to the present invention;

FIG. 10 is a side elevational view of the surgical sleeve shown in FIG. 9;

FIG. 11 is an enlarged view taken on the line 11—11 of FIG. 10;

FIG. 12 is a sectional view taken on the line 12—12 of FIG. 11;

FIG. 13 is an enlarged view taken on the line 13—13 of FIG. 12;

FIG. 14 is an enlarged bottom plan view of the vacuum sleeve shown in FIG. 9; and FIG. 15 is a sectional view of the surgical sleeve of the present invention as shown in FIGS. 9-14 but showing a portion of a curved resection instrument inserted therein.

Similar reference characters refer to similar parts throughout the several views of the drawings.

DETAILED DESCRIPTION

Figure 1:
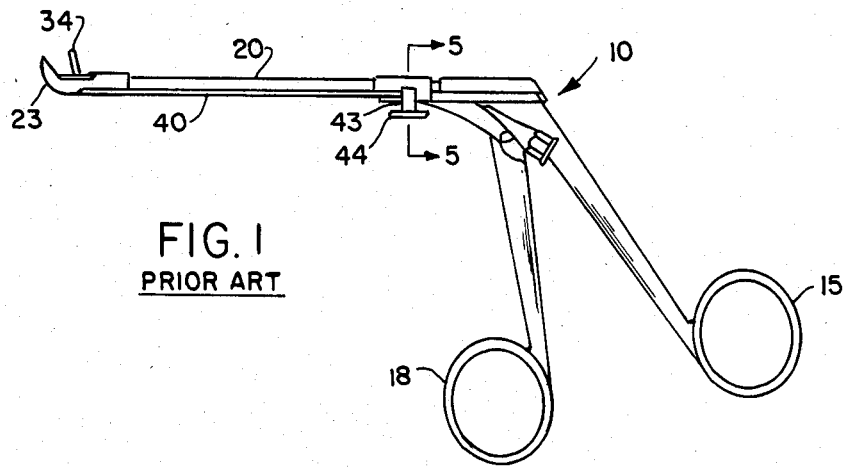
FIG. 1 is a side elevational view of a prior art surgical instrument for removing polyps from a nasal passage.
Figure 2:
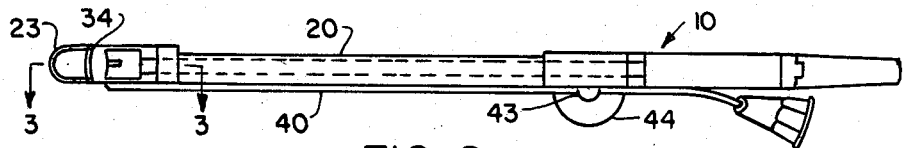
FIG. 2 is an enlarged top plan view of the surgical instrument shown in FIG. 1.
Figure 3:
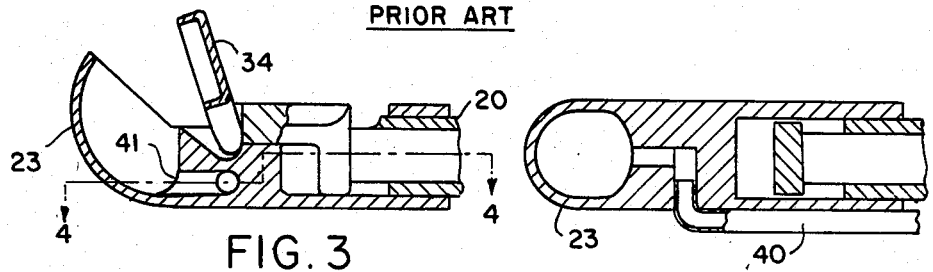
FIG. 3 is an enlarged sectional view of the cutter and jaw assembly taken on the line 3—3 of FIG. 2.
Figure 4:
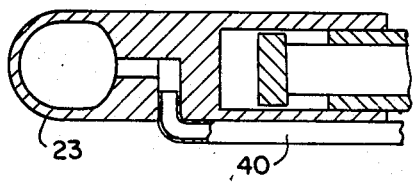
FIG. 4 is a sectional view taken on the line 4—4 of FIG. 3.

FIG. 1 is a side elevational view of a prior art surgical instrument generally designated 10 for enabling the removal of a polyp from a nasal passage of a patient. The instrument 10 includes a pair of scissor-like handles 15 and 18 respectively and an extension 20 having a cutter 34 pivotally mounted to the distal end thereof.

Figure 5:
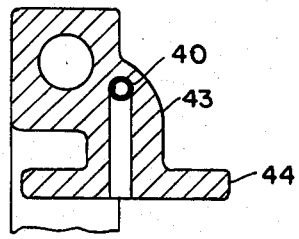
FIG. 5 is a sectional view taken on the line 5—5 of FIG. 1.

The cutter 34 cooperates with a stationary jaw 23 such that manipulation of the handles 15 and 18 results in pivotal movement of the cutter 34 relative to the jaw 23 for cutting the polyp away from the nasal passage. A flexible tube 40 extends from the jaw 23 towards the handles 15 and 18 where the tube 40 is connected to a source of vacuum. A finger-operated valve mechanism 43 and 44 shown in FIG. 5 enables the surgeon to selectively apply the source of vacuum to the vicinity of the jaw 23 such that when the vacuum source is applied, the polyp is drawn towards the jaw 23 thereby enabling the manually controlled cutter 34 to sever the polyp from the nasal passage. After severing the polyp from the nasal passage, the source of vacuum is released by the removal of the surgeons finger from the vacuum valve 43 and 44.

In the aforementioned prior art surgical instrument, the source of vacuum is used for manipulating movement of the tissue to be removed relative to the cutter but no disclosure is made of utilizing the vacuum source for constantly removing pieces of the removed tissue from the surgical site.

In the prior art, resection instruments have been developed including tubular extensions which enable removed tissue to be drawn from the vicinity of the cutter to a source of vacuum. Illustrative of such a prior art instrument is the suction pump shown in FIG. 8A and sold by Dyonics, Inc. Furthermore, the concept of applying a source of vacuum to the cutter by means of a rigid tubular member has been applied to the technique of surgical instruments having curved distal ends as shown in FIGS. 6–8.

Figure 6:
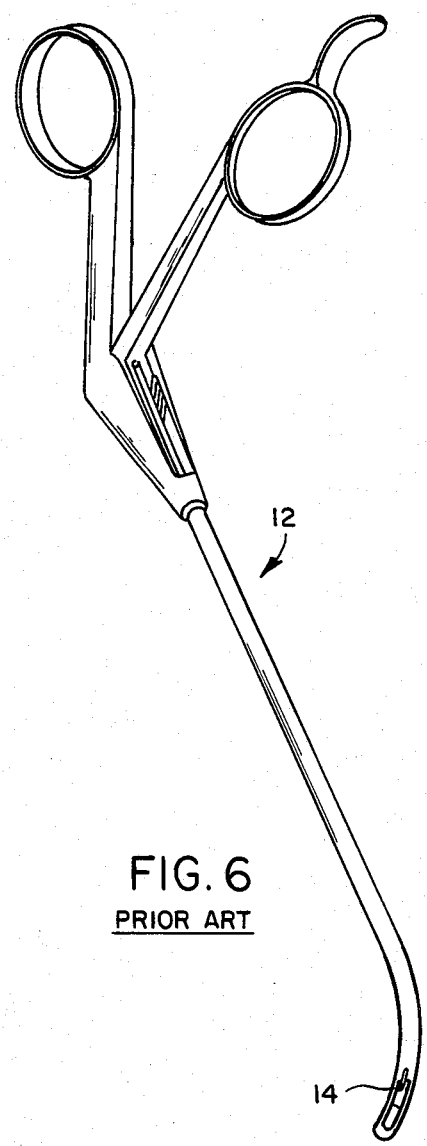
FIG. 6 is a perspective view of a prior art resection instrument having a curved distal end for enhancing access to the surgical site.
Figure 7:
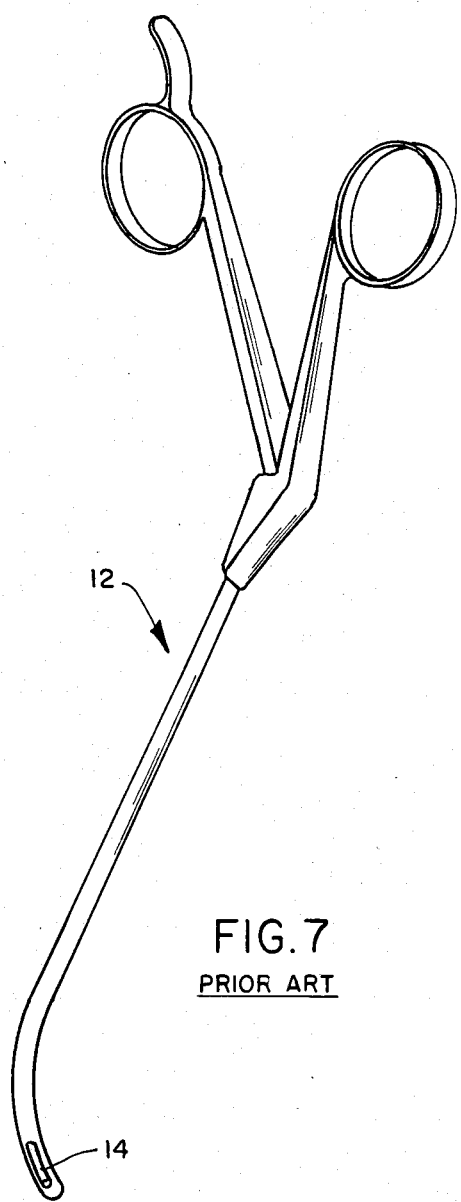
FIG. 7 is a similar view in reverse to that shown in FIG. 6.
Figure 8:
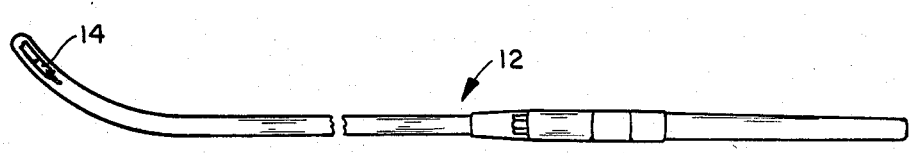
FIG. 8 is a side elevational view of the prior art surgical instrument shown in FIGS. 6 and 7.
Figure 8A:
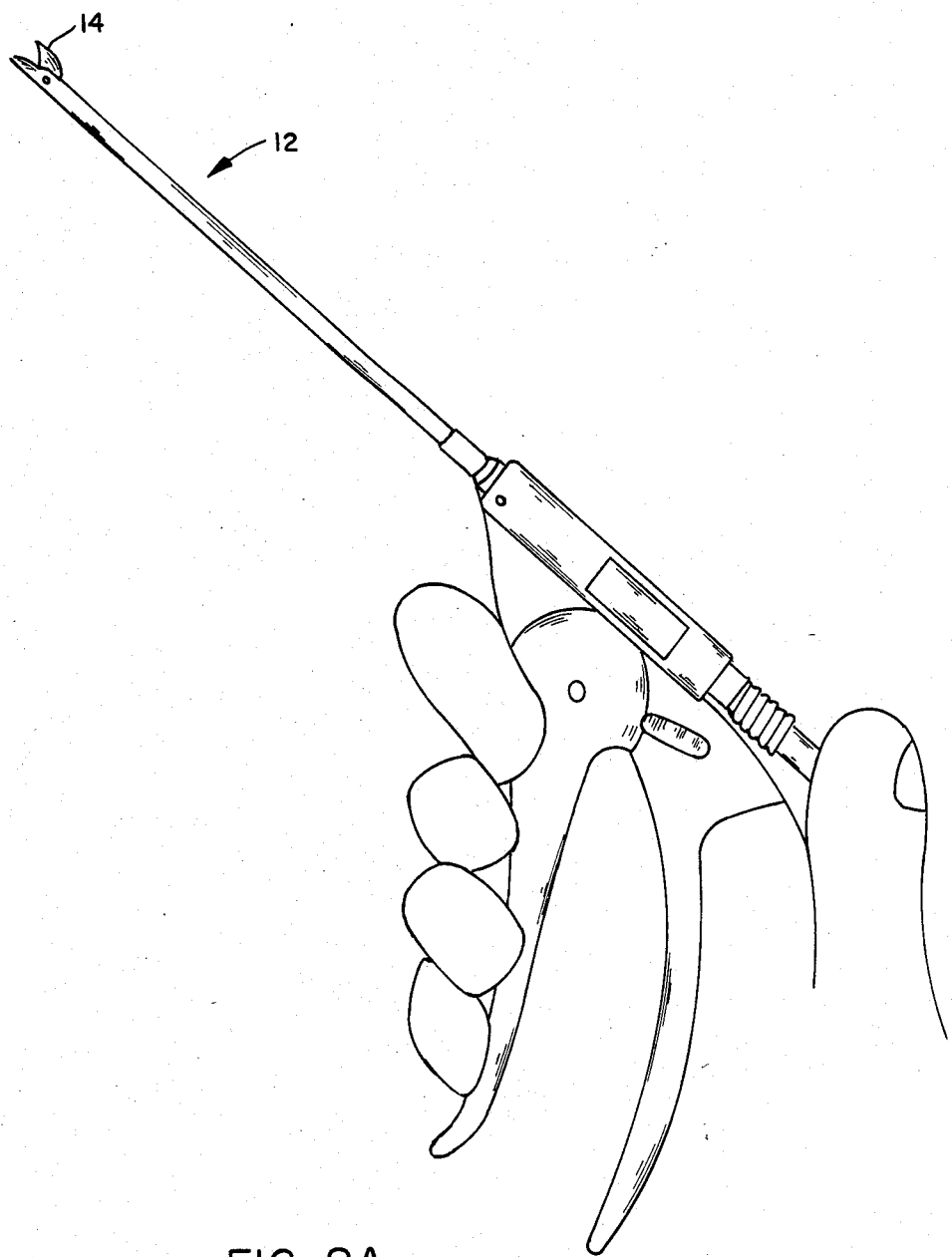
FIG. 8A is a perspective view of another prior art vacuum resection appliance.

However, as will be appreciated by those skilled in the art, the provision of a tubular extension for providing a vacuum passageway through the instrument is relatively complex particularly when applied to a surgical instrument having a curved configuration as shown in FIGS. 6–8. Furthermore, with instruments of a curved configuration as shown in FIGS. 6–8 it is the usual practice to equip a surgical theater with a large number of such curved instruments enabling the surgeon to gain ready access to the surgical site. Typically, a set of instruments, in addition to including a straight arthroscopic hook punch, will include a 30° and 45° right curved instrument in addition to a 30° and 45° left curved instrument. The manufacture of this basic five piece set including various relatively complex vacuum couplings has proved to be relatively expensive. The present invention overcomes the aforementioned problems by the provision of a flexible vacuum sleeve which extends over and frictionally engages a variety of differently curved standard hook punch forceps or resection instruments.

FIGS. 9–15 show the vacuum sleeve according to the present invention and generally designated 10 for removing severed tissue (not shown) from a surgical site (not shown). The vacuum sleeve 10 is used in conjunction with a surgical appliance 12 of the type shown in FIGS. 6, 7 and 8 having a cutting element 14, the vacuum sleeve 10 being connected to a vacuum source (not shown).

The vacuum sleeve 10 includes an elongated body member 16 having a distal end 18 and a proximal end 20. The body member 16 defines an internal passageway 22 shown in FIG. 13 which extends between the distal and proximal ends 18 and 20 respectively. The internal passageway 22 removably receives therein the surgical appliance 12. The distal end 18 of the body member 16 defines an aperture 24 shown in FIG. 11 such that when the surgical appliance 12 is disposed within the internal passageway 22, the cutting element 14 of the surgical appliance 12 extends through the aperture 24 as shown in FIG. 16 enabling the cutting element 14 to sever tissue from the surgical site. The internal passageway 22 which is of figure-8 cross-sectional configuration is connected to the vacuum source such that in use of the surgical appliance 12, when tissue is severed from the surgical site, the severed tissue is drawn from the surgical site through the aperture 24 and along the internal passageway 22 along the portion 22A of the passageway 22 towards the source of vacuum. The portion 22B accommodates the stem of the surgical appliance 12.

Preferably the body member 16 is flexible thereby accommodating a surgical appliance 12 having a curved configuration as shown in FIGS. 6–8 and the body member 16 is of plastics material having a unitary construction. The internal passageway 22 of the body member 16 is formed for frictionally receiving the surgical appliance 12 therein.

Aperture 24 of the vacuum sleeve 10 is disposed in a sidewall 26 of the body member 16 as shown in FIG. 12 and is located in proximity to the distal end 18 of the body member 16. Additionally, the vacuum sleeve 10 includes an input aperture 28 shown in FIG. 11 which is defined by the distal end 18 of the body member 16 for facilitating the flow of the tissue severed from the surgical site along the internal passageway 22 of the body member 16. Usually, when performing knee surgery, a liquid is injected into the surgical site in order to facilitate such operation. The provision of the input aperture 28 enables the establishment of the flow of the liquid and entrained tissue from the surgical site into the input aperture 28 and through the internal passageway 22 of the body member 16.

The vacuum sleeve includes an end wall 30 shown in FIG. 12 which is disposed in the distal end 18 of the body member 16 such that the aperture 24 is disposed in the sidewall 26 of the distal end 18 of the body member 16 and the input aperture 28 is disposed in the end wall 30 of the body member 16 for facilitating the flow of tissue severed from the surgical site along the portion 22A of the internal passageway 22 of the body member 16. The end wall 30 of the body member 16 forms an angle relative to the body member 16 to facilitate insertion of the vacuum sleeve 10 into the surgical site.

The proximal end 20 of the body member 16 defines a seal port 32 for receiving the surgical appliance 12 therein. The seal port 32 is flexible for resiliently engaging the surgical appliance 12 extending through the internal passageway 22 of the body member 16 at the proximal end 20 of the body member 16.

The vacuum sleeve 10 also includes a vacuum port 34 which is in fluid communication with both the portions 22A and 22B of the the internal passageway 22 of the body member 16. The vacuum port 34 is connectable to the vacuum source for removing tissue severed from the surgical site by drawing the removed tissue through the aperture 24 and along the portion 22A of the internal passageway 22 by the action of the vacuum source. A vacuum coupling means 36 couples the vacuum port 34 such that the vacuum port 34 which is in fluid communication with the vacuum source is connected to the portions 22A and 22B of the passageway 22. The seal port 32 provides a seal between the surgical appliance 12 and the body member 16 with the vacuum port 34 being disposed in the coupling means 36.

The body member 16 is flexible for frictionally receiving therein the surgical appliance 12 and the coupling means 36 is secured to the proximal end 20 of the body member 16 for forming a fluid tight seal thereby. The vacuum port 34 is disposed in the coupling means 36 and the seal port 32 is disposed in the coupling means 36 for forming a seal between the surgical appliance 12 and the coupling means 36. The coupling means 36 is a unitary flexible member having a greater resilience than the resiliency of the elongated body member 16.

As shown particularly with reference to FIG. 13, the internal passageway 22 of the body member 16 has a noncircular figure-8 crosssectional configuration for receiving therein the surgical appliance 12.

In use of the vacuum sleeve 10 of the present invention, when the surgeon has selected the particular resection instrument required to gain access to the surgical site, the coupling means 36 of the vacuum sleeve 10 is held by the surgeon between the thumb and forefinger and the distal end 18 of the surgical appliance 12 is threaded through the portion 22B of the passageway 22 until the cutting element 14 protrudes from the cutting aperture 24. Due to the flexibility of the vacuum sleeve 10, the sleeve 10 will assume the curved configuration of the surgical appliance inserted therein and the vacuum port 34 will then be connected to the source of vacuum. As the surgeon manipulates the finger and thumb ring of the surgical instrument, the cutting element 14 will pivot relative to the fixed jaw thereby severing tissue from the surgical site. Such severed tissue will be drawn away from the surgical site through the cutting aperture 24 towards the source of vacuum. The input aperture 28 establishes and maintains the flow of fluid from the surgical site towards the vacuum source regardless of the pivotal disposition of the cutter relative to the fixed jaw.

The flexible vacuum sleeve according to the present invention enables a plurality of variously curved resection instruments to be adapted to provide an efficient means for removing severed tissue from the surgical site thereby not only reducing the cost that would be involved in the provision of an individual vacuum tube for each instrument, but also providing a vacuum sleeve which may be discarded after each use thereby reducing the cost involved in sterilization and cleaning.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An adaptor vacuum sleeve for removing severed tissues from a surgical site for use with a self-contained cutting instrument having a cutting element and for connection to a vacuum source, comprising:
   an externally applied adapter sleeve means for removably receiving a self-contained cutting instrument;
   said adaptor sleeve means including an elongated body member having a distal end and a proximal end with an internal passageway means extending therebetween;
   said internal passageway means of said elongated body member being formed for receiving in use said self-contained cutting instrument therein;
   an aperture in said elongated body member enabling said cutting element of the cutting instrument in use to extend through said elongated body member to sever tissue from the surgical site;
   seal means located at said proximal end of said elongated body member for forming a seal between said cutting instrument and said elongated body member; and
   said seal means being flexible for resiliently engaging said self-contained cutting instrument at said proximal end of said elongated body member;
   a vacuum port in fluid communication with said internal passageway means of said elongated body member and being connectable to the vacuum source for removing tissue severed from the surgical site by drawing the removed tissue through said aperture and along said internal passageway means of said elongated member by action of the vacuum source.

2. A vacuum sleeve for removing severed tissue from a surgical site as set forth in claim 1, wherein said elongated body member is flexible for accommodating therein said cutting instrument having a curved configuration.

3. A vacuum sleeve for removing severed tissue from a surgical site as set forth in claim 1, wherein said elongated body member is constructed of a unitary plastic material.

4. A vacuum sleeve for removing severed tissue from a surgical site as set forth in claim 1, wherein said internal passageway means of said elongated body member is formed for frictionally receiving said cutting instrument therein.

5. A vacuum sleeve for removing severed tissue from a surgical site as set forth in claim 1, wherein said aperture is disposed in a sidewall of said elongated body member and located in proximity to said distal end of said elongated body member.

6. A vacuum sleeve for removing severed tissue from a surgical site as set forth in claim 1, including an input aperture disposed in said distal end of said elongated body member for facilitating the flow of the tissue severed from the surgical site along said internal passageway means of said elongated body member.

7. A vacuum sleeve for removing severed tissue from a surgical site as set forth in claim 1, including an input aperture disposed in said distal end of said elongated body member for facilitating the flow of the tissue severed from the surgical site along said internal passageway means of said elongated body member by establishing a flow of fluid from the surgical site into said input aperture and through said internal passageway means of said elongated body member.

8. A vacuum sleeve for removing severed tissue from a surgical site as set forth in claim 1, including an end wall disposed in said distal end of said elongated body member;
   said aperture being disposed in a sidewall at said distal end of said elongated body member; and
   an input aperture disposed in said end wall of said elongated body member for facilitating the flow of the tissue severed from the surgical site along said internal passageway means of said elongated body member by establishing a flow of fluid from the surgical site into said input aperture and through said internal passageway means of said elongated body member.

9. A vacuum sleeve for removing severed tissue from a surgical site as set forth in claim 1, wherein said end wall of said elongated body member forms an angle relative to said elongated body member to facilitate insertion of the vacuum sleeve into the surgical site.

10. A vacuum sleeve for removing severed tissue from a surgical site as set forth in claim 1, wherein said vacuum port includes vacuum coupling means for coupling said vacuum port to be in fluid communication with the vacuum source.

11. A vacuum sleeve for removing severed tissue from a surgical site as set forth in claim 1, including a seal port for forming a seal between said cutting instrument and said elongated body member.

12. A vacuum sleeve for removing severed tissue from a surgical site as set forth in claim 11, wherein said internal passageway means of said elongated body member has a noncircular cross-section for frictionally receiving said cutting instrument therein.

13. A vacuum sleeve for removing severed tissue from a surgical site as set forth in claim 11, wherein said internal passageway means of said elongated body member has a substantially figure-8 cross-section for receiving said cutting instrument therein.

14. A vacuum sleeve for removing severed tissue from a surgical site as set forth in claim 11, wherein said proximal end of said elongated body member defines a proximal end aperture for receiving the surgical appliance therein; and said seal port being flexible for resiliently engaging the surgical appliance extending through said internal passageway of said elongated body member at said proximal end of said elongated body member.

15. A vacuum sleeve for removing severed tissue from a surgical site as set forth in claim 1, including coupling means secured to said proximal end of said elongated body member;

said vacuum port being disposed in said coupling means; and a seal port disposed in said coupling means for forming a seal between said cutting instrument and said elongated body member.

16. A vacuum sleeve for removing severed tissue from a surgical site as set forth in claim 1, including a unitary coupling means secured to said proximal end of said elongated body member for forming a fluid tight seal thereby; and said vacuum port being disposed in said coupling means;

a seal port disposed in said coupling means for forming a seal between said cutting instrument and said coupling means.

17. A vacuum sleeve for removing severed tissue from a surgical site as set forth in claim 1, wherein:

said elongated body member being flexible for frictionally receiving therein said cutting instrument;

coupling means secured to said proximal end of said elongated body member for forming a fluid tight seal thereby;

said vacuum port being disposed in said coupling means;

a seal port disposed in said coupling means for forming a seal between said cutting instrument and said coupling means;

said coupling means being a unitary flexible member preferably having a greater resilience than said elongated body member.

18. A vacuum sleeve for removing severed tissue from a surgical site as set forth in claim 1, wherein said elongated body member is flexible for accommodating therein said cutting instrument having a curved configuration.

* * * * *